United States Patent [19]

McDaniel

[11] Patent Number: 4,902,816
[45] Date of Patent: Feb. 20, 1990

[54] POLYOLS FROM PHTHALIC COMPOUNDS

[75] Inventor: Kenneth G. McDaniel, West Chester, Pa.

[73] Assignee: ARCO Chemical Technology, Inc., Wilmington, Del.

[21] Appl. No.: 173,788

[22] Filed: Mar. 28, 1988

[51] Int. Cl.$^4$ .................. C07C 67/03; C07C 67/08; C07C 69/80

[52] U.S. Cl. .................. 560/88; 521/172; 521/173; 521/175; 560/91; 560/93

[58] Field of Search .................. 560/88, 91, 93

[56] References Cited

U.S. PATENT DOCUMENTS

| | | | |
|---|---|---|---|
| 4,092,276 | 5/1978 | Narayan | 521/172 |
| 4,469,824 | 9/1984 | Grigsby et al. | 521/173 |
| 4,544,679 | 10/1985 | Tideswell et al. | 521/116 |
| 4,595,711 | 6/1986 | Wood | 521/158 |
| 4,642,319 | 2/1987 | McDaniel | 521/175 |
| 4,644,019 | 2/1987 | McDaniel | 521/173 |
| 4,644,027 | 2/1987 | Magnus et al. | 524/375 |

*Primary Examiner*—Werren B. Lone
*Assistant Examiner*—Vera C. Clarke
*Attorney, Agent, or Firm*—David L. Mossman; Steve Rosenblatt

[57] ABSTRACT

Polyols containing polyether and polyester moieties, based on phthalic acid are described. A phthalic acid derivative is reacted with a polyether polyol to give the novel polyols which are useful not only in polyisocyanurate foams, but also polyurethane foams as well. The phthalic acid derivative may be phthalic acid, phthalic anhydride and an ester of phthalic acid, for example. The polyester polyol is made from an initiator selected from the group consisting of alkanolamines, alkyleneamines, arylamines, sucrose, glycerin, sorbitol, α-methylglucoside, β-methylglucoside, and mixtures thereof. The polyester polyol may be made by alkoxylating the initiators.

22 Claims, No Drawings

POLYOLS FROM PHTHALIC COMPOUNDS

FIELD OF THE INVENTION

The invention relates to methods for preparing polyols and more particularly relates to methods for preparing polyols useful in preparing polyurethane and polyisocyanurate foams, where the polyols are derived from phthalic acid derivatives.

Background of the Invention

It is known to prepare polyurethane foam by the reaction of a polyisocyanate, a polyol and a blowing agent, such as a halogenated hydrocarbon, water or both, in the presence of a catalyst. One particular area of polyurethane technology is based on rigid polyurethane foams.

U.S. Pat. No. 4,469,824 to Grigsby, et al., issued Sept. 4, 1984, describes polyols produced by reacting scrap polyethylene terephthalate (PET) with diethylene glycol and one or more oxyalkylene glycols and stripping out some of the ethylene glycol present. The mole ratio of glycols to scrap PET is greater than 1.2:1. These polyols are reacted with a polyisocyanate to produce polyurethane foams.

Rigid foams generally have good insulative properties and are thus desirable for use in building insulation. As with all building materials, it is desirable to provide rigid foams that are as fire resistant as possible. One approach to this goal is to modify the polyol.

Polyisocyanurate foams are a type which are considered to be fire resistant and show low smoke evolution on burning. However, polyisocyanurate foams tend to be brittle or friable. Various types of polyols have been devised to lower the foam friability, but what frequently happens is that the fire and smoke properties of the polyisocyanurate foam deteriorate. Thus, a fine balance exists between the amount and type of polyol one adds to a polyisocyanurate foam formulation in order to maintain maximum flame and smoke resistance while at the same time reach a improvement in foam friability. U.S. Pat. Nos. 4,039,487 and 4,092,276 describe attempts at this fine balance, although each has its disadvantages.

Scrap polyalkylene terephthlate, such as scrap PET, is known to be incorporated into polyurethanes. For example, U.S. Pat. No. 4,048,104 teaches that polyisocyanate prepolymers for use in polyurethane products may be prepared by combining an organic polyisocyanate with polyols which are the hydroxyl-terminated digestion products of waste polyalkylene terephthalate polymers and organic polyols. A polyol ingredient which is the digestion product of polyalkylene terephthalate residues or scraps digested with organic polyols is also described in U.S. Pat. No. 4,223,068. Another example where terephthalic acid residues are employed is outlined in U.S. Pat. No. 4,246,365 where polyurethanes are made from polyesters containing at least two hydroxyl groups and terephthalic acid residues.

In U.S. Pat. No. 4,237,238 a polyol mixture is prepared by the transesterification of a residue from the manufacture of dimethyl terephthlate with a glycol, which is then used to produce polyisocyanurate foams having a combination of a high degree of fire resistance with low smoke evolution, low foam friability and high compressive strength. The preparation of such a polyol mixture, such as from ethylene glycol and dimethyl terephthalate esterified oxidate residues, is described in U.S. Pat. No. 3,647,759. J. M. Hughes and John Clinton, in the Proceedings of the S.P.I. 25th Annual Urethane Division Technical Conference, Scottsdale, Ariz. October, 1979, describe other foams prepared from the polyols of U.S. Pat. No. 3,647,759.

Another type of polyisocyanurate foam employs a polyol blend using both amide diols and primary hydroxyl polyols to give a foam having a high reaction exotherm, making it particularly suited to the preparation of polyisocyanurate foam laminates, according to U.S. Pat. No. 4,246,364.

However, another major factor with the use of the polyester polyols described above in producing foams is that they have a limited solubility in the widely used halogenated hydrocarbon blowing agents, such as fluorocarbon 11, which is used to expand the foam and provide its insulating characteristics. It would be beneficial if a procedure could be found by which these polyester polyols could be made more soluble in halogenated hydrocarbon blowing agents.

Other methods are known for increasing the solubility of these polyester polyols in halogenated hydrocarbon blowing agents. For example, U.S. Pat. No. 4,642,319 describes modifying recycled polyethylene terephthalate polyols with aromatic amino polyols, sucrose polyols, ethoxylated alpha-methyl glucosides, alkoxylated glycerine or alkoxylated sorbitol. Additionally, U.S. Pat. No. 4,644,019 teaches modifying a recycled polyethylene terephthalate polyol with polyethoxylated nonlyphenol to increase halogenated hydrocarbon solubility. However, a disadvantage with using the ethoxylates of nonylphenol is that the ethoxylate is monofunctional, that is, a monofunctional polyester is created. This polyester would act as a chain stopper during a polymerization reaction, which is not desired. Further, U.S. Pat. No. 4,529,744 shows that compatibility agents and polyol blend compositions may be provided containing nonionic block ethoxylate propoxylate compounds, amine and amine diol compounds, and aromatic ester polyols, especially phthalate polyester polyols, which blends are miscible with fluorocarbon blowing agents.

Polyol blend compositions containing nonionic ethoxylate propoxylate compounds and aromatic ester polyols, especially phthalate polyester polyols, which blends are miscible with fluorocarbon blowing agents are taught in U.S. Pat. No. 4,595,711. U.S. Pat. No. 4,644,027 describes phthalate polyester polyols containing reaction products of a phthalic acid compound, a low molecular weight diol compound and a hydrophobic compound are provided which are compatibilized with fluorocarbon blowing agents and which possess a variety of other desirable characteristics. Other patents which teach self-compatibilizing phthlate-based polyester polyols include U.S. Pat. Nos. 4,644,047 and 4,644,048.

Many other types of polyols useful in the production of polyurethane or polyisocyanurate are known. For example, U.S. Pat. No. 4,526,908 describes homogeneous liquid polyol blend compositions containing (a) certain aliphatic polyols, (b) phthalate diester polyols of these aliphatic polyols, and (c) trimellitate polyols of the same aliphatic polyols. The resulting polyol blend compositions are useful in making homogeneous liquid resin prepolymer blends compositions containing, in addition to such a polyol blend, a fluorocarbon blowing agent, a cell stabilizing surfactant, and a urethane and/or isocyanurate catalyst. Finally, a unique polyol blend of four components is outlined in U.S. Pat. No. 4,544,679 having (a) 30 to 90 wt.% of a polyester diol having an OH number of from about 50 to about 500, (b) 2 to 40 wt.% of an organic compound containing from 3 to 8 hydroxyl groups, (c) 5 to 30 wt.% of a condensation product formed from 1 mole of a phenol and from 4 to 15 moles of ethylene oxide, and (d) 0 to 40 wt.% of another diol.

Phthalic acid esters made with diethylene glycol are widely used in isocyanurate foams, such as in panel line applications. However, the low functionality of this type of product limits it use in polyurethane foams. It would be advantageous if a polyester polyol could be developed which would provide good properties for both polyisocyanurate and polyurethane foams.

SUMMARY OF THE INVENTION

Accordingly, it is an object of the present invention to provide a new class of polyols useful in the preparation of both polyurethane and polyisocyanurate foams.

It is another object of the present invention to provide a new class of polyols which will provide polyurethane foams with good dimensional stability and K-factors.

It is yet another object of the invention to provide a new class of polyols which will provide polyisocyanurate foams with good performance in small scale burn tests.

In carrying out these and other objects of the invention, there is provided, in one form, a method for preparing polyols useful in the preparation of polyurethane and polyisocyanurate foams. The method involves reacting a phthalic acid derivative with a polyether polyol, where the phthalic acid derivative is selected from the group consisting of phthalic acid, phthalic anhydride and an ester of phthalic acid and where the polyether polyol is made from an initiator selected from the group consisting of alkanolamines, alkyleneamines, arylamines, sucrose, glycerin, sorbitol, methylglucoside, resins of phenol, aniline and mixed phenol aniline Mannich condensates, and mixtures thereof.

DETAILED DESCRIPTION OF THE INVENTION

It has been discovered that novel, useful polyols may be prepared by reacting phthalic acid derivatives with various polyether polyols. These new polyols are used in preparing both improved polyurethane foams and improved isocyanurate foams. The resulting foams exhibit good dimensional stability and good K-factors. The isocyanurate foams give good performance in small scale burn tests. These new polyols contain both polyether and polyester groups, and are based on phthalate acid derivatives.

These polyols may be prepared by several different methods.

Method 1. Phthalic anhydride may be reacted with a polyether to form an intermediate acid ester which is alkoxylated with an alkylene oxide or an alkylene carbonate, such as propylene oxide or propylene carbonate, for example.

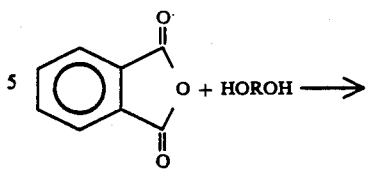

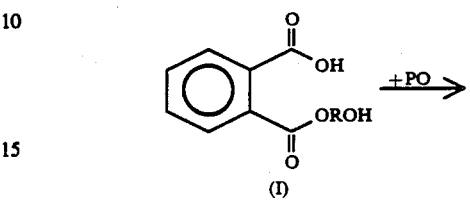

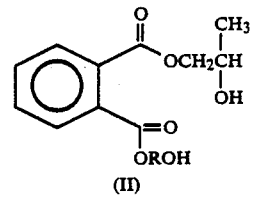

In this method and subsequent methods, the compound HOROH will be taken to be a di- or higher hydroxyl compound. The R group symbolizes a variety of moieties, such as alkanolamine, alkyleneamine, aryl or aromatic amine, sucrose, glycerin, sorbitol, α-methylglucoside, β-methylglucoside and mixtures thereof. Examples of a suitable alkanolamine would include, but are not limited to, diethanolamine, dipropanolamine, and the like. A suitable arylamine would be toluenediamine, for example. An aromatic amino polyol based on a Mannich condensate of nonylphenol, formaldehyde, and diethanolamine is also suitable. The HOROH polyether polyol should have at least two reactive -OH groups present and a polyether moiety, that is, more than one ether moiety in the molecule. For example, the HOROH polyether polyol could be alkoxylated sucrose, sorbitol, glycerin, methylglucoside, alkanolamines, alkoxylated aliphatic amines such as propoxylated 1,3-propanediamines, alkoxylated ethyleneamines and propylene amines such as diethylenetriamine and the like, alkoxylated arylamines such as 1,4-diaminobenzene and the like, alkoxylated resins of phenol, aniline, and mixed phenol aniline like methylenedianiline or bisphenol A, and alkoxylated Mannich condensates.

Method 2. Phthalic anhydride may be reacted with two moles of the polyether polyol per mole of anhydride with the removal of water, as symbolically represented:

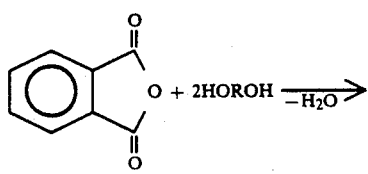

-continued

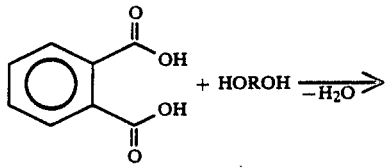
(III)

Method 3. Phthalic acid may be reacted with one mole of polyol with removal of water and then with an alkylene oxide or an alkylene carbonate, as illustrated:

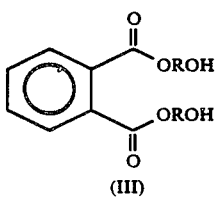

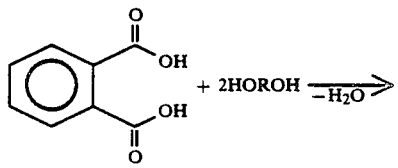
(I)

(II)

Method 4. Phthalic acid may be reacted with two moles of polyol with the removal of water during the reaction:

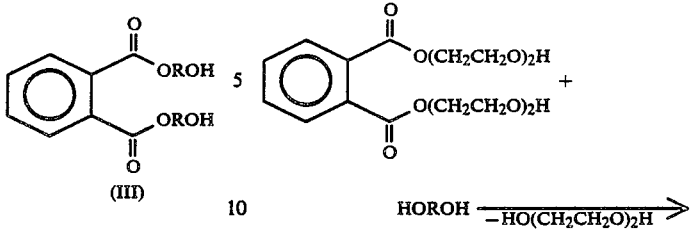

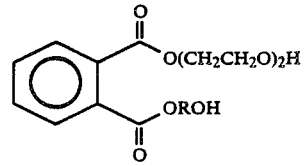

It will be appreciated that the reactions given herein are simplified. For example, one contemplated reaction may be diagrammed in simplified form as:

(IV)

Whereas, in actuality, an equilibrium exists between the following compounds, where y=0, 1, 2 or 3:

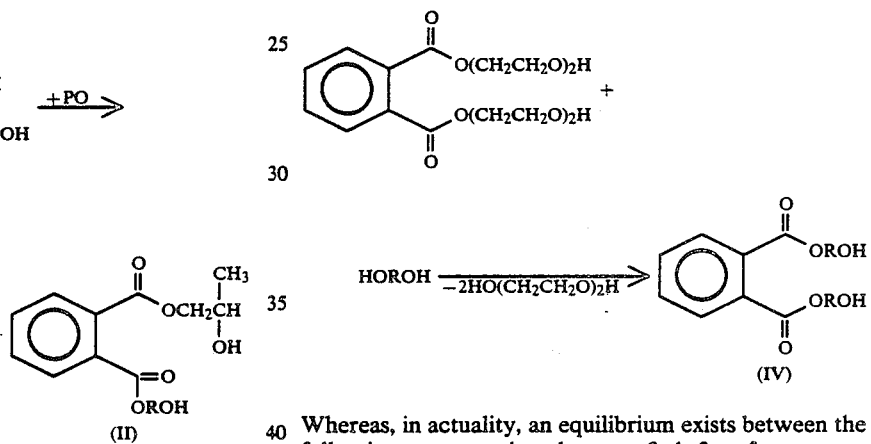

(III)

Method 5. An ester of phthalic acid reacted with one or two moles of a polyol, with the removal of glycol or alcohol to produce the modified polyester polyol useful in the production of foams:

The equilibrium product would become more complicated as the functionality of the polyol reactant increased. In addition, the molar ratio of the phthalic moiety to polyol does not have to be 1:1. For example, the moles of phthalic residue per mole of polyether polyol may be small or greater than one.

On the other hand, the functionalities preferably should not be equal. That is, the reactive ester groups should not equal the reactive hydroxyl groups. This reactive group ratio of polyester:polyol may range from 0.10:1.0 to 0.5:1.0. For example, it is within the scope of this invention to react one mole of a polyester of 3 to 4 functionality with a polyol of 8 functionality.

The polyether polyol component has already been described. Generally, it is derived from an initiator such as alkanolamine, alkylamine, aryl or aromatic amine, sucrose, glycerin, sorbitol, α-methylglucoside, β-methylglucoside or other methylglucoside, resins of phenol, aniline and mixed phenol aniline, like methylenedianiline or bisphenol A, Mannich condensates, and mixtures thereof. Examples of a suitable initiator would include, but are not limited to, diethanolamine, dipropanolamine, toluenediamine, and the like. The polyether polyol component can be made by alkoxylating the initiator with a desired number of moles of an alkylene oxide. Preferably, the alkylene oxide has two to four carbon atoms, and is thus, ethylene oxide, propylene oxide, butylene oxide or mixtures of the oxides.

The phthalic acid derivative component may be phthalic acid, phthalic anhydride, or an ester of phthalic acid, and may be represented as:

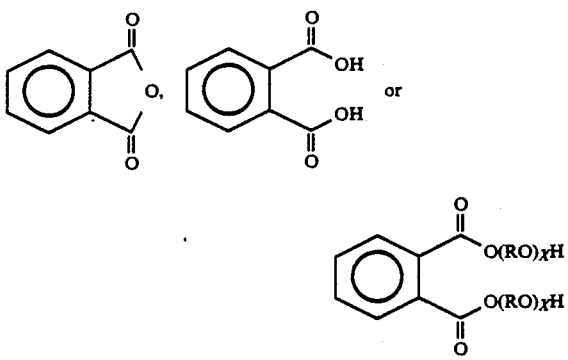

where in the ester compound, R is an alkylene moiety of from two to four carbon atoms, and x ranges from 1 to 4, or R is an alkyl moiety, preferably an alkyl moiety of 1 to 4 carbon atoms.

The reaction of the phthalic acid derivatives with the polyether polyols may be conducted in the absence of a catalyst at a temperature ranging from about 130° to 220° C., preferably from about 160° to 210° C. The reaction may be performed at a pressure ranging from about atmospheric to about 5 mm Hg, preferably from atmospheric to about 10 mm Hg. It will be appreciated that one skilled in the art could conduct the inventive reaction at many different pressures, and that the reaction pressure is not crucial to the invention.

The invention will be illustrated further with respect to the following examples, which are not intended to limit the scope of the invention.

EXAMPLE 1

Procedure based on phthalic anhydride: Quantities of 360 grams (2.2 moles) of a 1.1 mole propylene oxide adduct of diethanolamine and 296 grams of phthalic anhydride were charged to a flask equipped with temperature control, a cooling unit, and the stirrer. The contents of the flask were heated in the ranged from 130° C. to 160° C. for 1.5 hours. At 105° C. to 120° C., 232 grams of propylene oxide and 1 g. of dimethylcylohexylamine were charged. The reactants were digested and excess propylene oxide was stripped to yield a polyol (Polyol A) with the following analyses:
OH number 428 mg KOH/g. polyol
Acid number: 0.6 mg KOH/g. polyol
$H_2O$: 0.085%
Amine: 273 meq/g
Viscosity: 63,800 cs at 25° C.

EXAMPLE 2

Procedure based on a phthalic ester: A polyester prepared from one mole of phthalic anhydride and 2 moles of diethylene glycol was used to prepare the modified polyester. Quantities of 465 g. of the polyester and 285 grams of an alkanolamine, prepared from diethanolamine and propylene oxide (2 moles), and 0.5 g zinc acetate were charged to a flask equipped with a heating mantle, a temperature controller, a distillation head, and vacuum capability. The contents of the flask were heated to 190° C. and 76 grams of diethylene glycol were removed using a vacuum. Fifteen grams of ethylene carbonate was charged to the flask, and the contents were cooled to 120° C. The flask was evacuated to remove any excess ethylene carbonate. The resulting polyol, designated Polyol B, had the following analyses:
OH number: 397 mg KOH/g. polyol
Acid number: 0.52 mg KOH/g. polyol
Amine: 1.83 meq/g
Viscosity: 2,568 cs at 25° C.

EXAMPLE 3

A polyol was prepared as in Example 2, except that 306 g. of the polyester of Example 2 and 494 g. of a polyether polyol based on a mixture of sucrose and glycerin, having an OH number of 520 were used as the reactants. The product, designated Polyol C had the following properties.
OH number: 432 mg KOH/g. polyol
Acid number: 2.13 mg KOH/g. polyol
Viscosity: 8,819 cs at 25° C.

EXAMPLE 4

Example 2 was repeated, except that 356 g. of the polyester and 429 g. of an aromatic aminopolyol based on Mannich condensate of nonylphenol, formaldehyde, and diethanolamine were used. A quantity of 51 ml of diethylene glycol was removed during the reaction. The resulting polyol, Polyol D, had the following analyses:
OH number: 324 mg KOH/g. polyol
Acid number: 0.8 mg KOH/g. polyol
Amine: 1.69 meq/g
Viscosity: 14,854 cs at 25° C.

EXAMPLE 5

This example illustrates the preparation of a polyol of this invention using a polyester containing 2 moles of an alkanolamine per mole of phthalic ester. Example 2 was repeated, except that 554 g. of the polyester and 436 g. of an alkanolamine prepared by the reaction of diethanolamine and 2 moles of propylene oxide. During the reaction, 200 g. of diethylene glycol were stripped. The resulting Polyol E had the following properties:
OH number: 392 mg KOH/g. polyol
Acid number: 5.53 mg KOH/g. polyol
Amine: 2.79 meq/g
Viscosity: 7742 cs at 25° C.

EXAMPLE 6

The procedure of Example 2 was repeated, except that 378 g. of the polyester and 442 g. of a polyether polyol prepared by the reaction of α-methylglucoside (1 mole) with propylene oxide (2 moles) and ethylene oxide (2 moles) were used. During the reaction, 56.23 g. of diethylene glycol was removed to give Polyol F with the following properties:

OH number: 441 mg KOH/g. polyol
Acid number: 1.6 mg KOH/g. polyol
Viscosity: 4499 cs at 25° C.

EXAMPLE 7

Once again, the procedure of Example 2 was repeated, except that 306 g. of the polyester and 494 g. of a polyether polyol prepared by reacting toluene diamine blocks of ethylene oxide and propylene oxide were employed. The polyether polyol had an OH no. of 390. Diethylene glycol (45.5 g.) was removed from the reaction to yield Polyol G:

OH number: 324 mg KOH/g. polyol
Acid number: 0.3 mg KOH/g. polyol
Viscosity: 1512 cs at 25° C.

Foams were prepared by a hand-mix technique, and these foams were poured into a box and allowed to cure. Data is given for both polyurethane foams and polyisocyanurate foams. The preparation of these types of foams is well-known in the art. Generally, the polyols of this invention are reacted with a polyisocyanate in the presence of a catalyst, either a polyurethane or polyisocyanurate catalyst, depending on the type of foam desired. Other components, such as blowing agents or surfactants, may be employed to enhance the properties of the foams, as desired. It is anticipated that one skilled in the art may optimize the foam formulations in which the polyols of the invention may be used.

TABLE I

| | Polyurethane Foams | | | | |
|---|---|---|---|---|---|
| | 1 | 2 | 3 | 4 | 5 |
| Formulations, pbw | | | | | |
| Polyol H* | 8.8 | 9.0 | 8.7 | 13.6 | 9.0 |
| Polyol A | 26.3 | — | — | — | — |
| Polyol B | — | 27.05 | — | — | — |
| Polyol C | — | — | 26.28 | — | — |
| Polyol D | — | — | — | 25.18 | — |
| Polyol E | — | — | — | — | 27.1 |
| DC-193 | 0.4 | 0.4 | 0.4 | 0.4 | 0.4 |
| Water | 0.3 | 0.3 | 0.3 | 0.3 | 0.3 |
| THANCAT ® TD-20 | 0.1 | 0.1 | 0.1 | 0.1 | 0.1 |
| Fluorocarbon 11 | 11.6 | 11.6 | 11.6 | 11.6 | 11.6 |
| Rubinate ® M | 52.5 | 51.55 | 52.42 | 48.62 | 51.5 |
| Reaction Profile | | | | | |
| Cream time (sec) | 16 | 9 | 11 | 6 | 7 |
| Gel time (sec) | 46 | 25 | 32 | 15 | 24 |
| Tack free time (sec) | 60 | 33 | 45 | 17 | 30 |
| Rise time (sec) | 93 | 56 | 69 | 34 | 51 |
| Foam Properties | | | | | |
| Density, pcf | 1.67 | 1.62 | 1.79 | 1.81 | 1.76 |
| K factor (BTU-in.)/(hr.-ft$^2$-°F.) | 0.106 | 0.113 | 0.103 | 0.106 | 0.108 |
| Compressive Strength, psi | 45.3 | 41 | 41.5 | 43.3 | 44.0 |
| Closed cells, % | 94.7 | 94.2 | 94.4 | 93.3 | 94.5 |
| Dimensional stability | | | | | |
| % change | ΔV | ΔV | ΔV | ΔV | ΔV |
| 158° F., 1 week | 2.5 | 2.7 | 2.9 | 4.4 | 3.7 |
| 95% R.H., 4 weeks | 3.9 | 4.7 | 5.3 | 9.3 | 5.8 |

*A polyol based on ethylene diamine, propylene oxide, and ethylene oxide with an hydroxyl number of 780.

TABLE II

| | Polyisocyanurate Foams | | | |
|---|---|---|---|---|
| | 6 | 7 | 8 | 9 |
| Formulations, pbw | | | | |
| Polyol A | 21.93 | — | — | — |
| Polyol C | — | 21.84 | — | — |
| Polyol D | — | — | 28.6 | — |
| Polyol E | — | — | — | 23.2 |
| Surfonic ® N-95 | 3.87 | 3.86 | — | 4.1 |
| DC-193 | 0.6 | 0.6 | 0.6 | 0.6 |
| Water | 0.5 | 0.5 | 0.5 | 0.5 |
| Hexchem ® 977 | 0.1 | 0.1 | 0.1 | 0.1 |
| Fluorocarbon 11 | 13.5 | 13.5 | 13.5 | 13.5 |
| Dimethylcyclohexylamine | 0.1 | 0.2 | 0.1 | 0.1 |
| Rubinate ® M | 59.5 | 59.6 | 56.7 | 58.0 |
| Index | 2.5 | 2.5 | 2.5 | 2.5 |
| Foam Properties | | | | |
| Density, pcf | 1.5 | 1.75 | 1.95 | 1.58 |
| K factor (BTU-in.)/(hr.-ft$^2$-°F.) | 0.107 | 0.126 | — | 0.113 |
| Compressive Strength, psi | 30 | 25.8 | 37.4 | 26.6 |
| Friability, % | 8.3 | 13.6 | 12.3 | 9.7 |
| Closed cells, % | 93.6 | 89.4 | 94.2 | 91.8 |
| Dimensional stability | | | | |
| % change, 4 weeks | ΔV | ΔV | ΔV | ΔV |
| 158° F., 95% R.H. | 7.7 | 8.1 | 11.1 | 10.1 |
| 95% R.H. | | | | |
| Butler Chimney Test | | | | |
| % wt. retained | 69.9 | 79.9 | 82.9 | 74.9 |

GLOSSARY

| | |
|---|---|
| Freon R-11A | Fluorocarbon 11, made by E. I. du Pont de Nemours, Co. |
| Hexchem ® 977 | Potassium octoate in glycol; available from Mooney Chemical Co. |
| R.H. | Relative humidity |
| Rubinate ® M | A 2.7 functional aromatic isocyanate made by Rubicon Chemical Co. |
| Silicone DC-193 ® | A silicone surfactant made by Dow-Corning Corp. |
| Surfonic ® N-95 | The 9.5 molar ethoxylate of nonylphenol, sold by Texaco Chemical Co. |
| THANCAT ® TD-20 | 80 wt. % dimethylamine, 20 wt. % triethylenediamine, made by Texaco Chemical Co. |

The polyols of this invention have increased functionality over other polyester polyols, for example, phthalic acid esters made from diethylene glycol, that are widely used in isocyanurate foams for panel applications, but cannot be used effectively in polyurethane foams. As shown in Tables I and II, the foams made from the novel polyester polyols of this invention exhibit good dimensional stability and K-factors in both polyurethane and polyisocyanurate foams. The isocyanurate foams give good performance in small scale burn tests (Butler Chimney Tests).

Many modifications may be made in the polyester polyols of this invention and their method of production without departing from the spirit and scope of the invention, which is defined only in the appended claims. For example, one skilled in the art could adjust the temperature, pressure, reactants, proportions and modes of additions to provide polyester polyols that give foams with optimal properties.

I claim:

1. A method for preparing a polyol useful in the preparation of both polyurethane and polyisocyanurate foams, comprising reacting a phthalic acid derivative with a polyether polyol, where the phthalic acid derivative is selected from the group consisting of phthalic acid, phthalic anhydride and an ester of phthalic acid and where the polyether polyol is made from an initiator selected from the group consisting of an alkanolamine, an alkyleneamine, an arylamine, sucrose, glycerin, sorbitol, a methylglucoside, a resin of phenol, aniline and phenol aniline, a Mannich condensate and mixtures thereof.

2. The method of claim 1 wherein the polyether polyol is made by reacting the initiator with an alkylene oxide.

3. The method of claim 2 wherein the alkylene oxide reacted with the initiator to make the polyether polyol is selected from the group consisting of ethylene oxide, propylene oxide, butylene oxide and mixtures thereof.

4. The method of claim 1 additionally comprising a step of adding an alkylene oxide or alkylene carbonate, of 2 to 4 carbon atoms, to the polyol after the reaction of the phthalic acid derivative with the polyether polyol.

5. The method of claim 1 wherein the reaction is conducted at a temperature in the range of about 130° to 220° C.

6. A method for preparing a polyol useful in the preparation of both polyurethane and polyisocyanurate foams, comprising reacting a phthalic acid derivative selected from the group consisting of

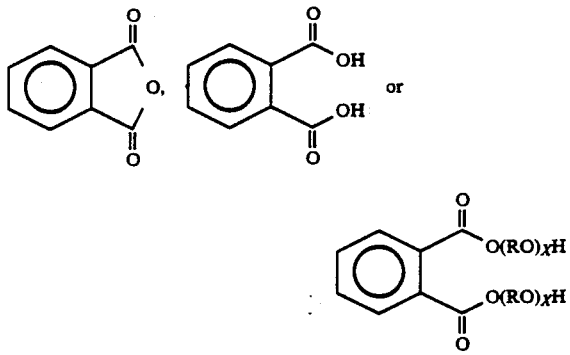

where R is an alkylene moiety of from 2 to 4 carbon atoms, or R is an alkyl moiety, and x ranges from 1 to 4, with a polyether polyol made from an initiator selected from the group consisting of an alkanolamine, an alkyleneamine, an arylamine, sucrose, glycerin, sorbitol, a methylglucoside, a resin of phenol, aniline, methylenedianiline, bisphenol A and phenol aniline, a Mannich condensate, and mixtures thereof.

7. The method of claim 6 wherein the polyether polyol is made by reacting the initiator with an alkylene oxide.

8. The method of claim 7 wherein the alkylene oxide reacted with the initiator to make the polyether polyol is selected from the group consisting of ethylene oxide, propylene oxide, butylene oxide and mixtures thereof.

9. The method of claim 6 wherein the reaction is conducted at a temperature in the range of about 130° to 220° C.

10. The method of claim 6 wherein the initiator for the polyether polyol is selected from the group consisting of an alkylene oxide adduct of an alkanolamine, an ethyleneamine, a propyleneamine, diethylenetriamine, toluenediamine, 1,4-diaminobenzene, sucrose, glycerin, sorbitol, α-methylglucoside, β-methylglucoside, a resin of phenol, a resin of aniline, a Mannich condensate and mixtures thereof.

11. The method of claim 6 additionally comprising a step of adding an alkylene oxide or alkylene carbonate, of 2 to 4 carbon atoms, to the polyol after the reaction of the phthalic acid derivative with the polyether.

12. A method for preparing a polyol useful in the preparation of both polyurethane and polyisocyanurate foams, comprising
reacting a phthalic acid derivative with a polyether polyol where the phthalic acid derivative is selected from the group consisting of phthalic acid and phthalic anhydride and where the polyether polyol is made by alkoxylating an initiator selected from the group consisting of an alkanolamine, an alkyleneamine, an arylamine, sucrose, glycerin, sorbitol, a methylglucoside, a resin of phenol, aniline and phenol aniline, a Mannich condensate, and mixtures thereof, to give an intermediate compound; and
reacting the intermediate compound with an alkylene oxide or an alkylene carbonate to give the polyols useful in preparing foams.

13. A method for preparing a polyol useful in the preparation of both polyurethane and polyisocyanurate foams, comprising reacting one mole of a phthalic acid derivative with two moles of a polyether polyol where the phthalic acid derivative is selected from the group consisting of phthalic acid and phthalic anhydride and where the polyether polyol is made by reacting an alkylene oxide with an initiator selected from the group consisting of an alkanolamine, an alkyleneamine, an arylamine, sucrose, glycerin, sorbitol, α-methylglucoside, β-methylglucoside, a resin of phenol, a resin of aniline, a resin of methylenedianiline, a resin of bisphenol A, a Mannich condensate and mixtures thereof.

14. A method for preparing a polyol useful in the preparation of both polyurethane and polyisocyanurate foams comprising reacting an ester of phthalic acid having the formula:

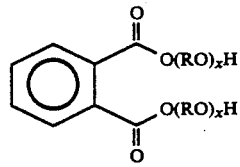

where R is an alkylene group of 2 to 4 carbon atoms, or R is an alkyl moiety, and x ranges from 1 to 4, with a polyether polyol, where the polyether polyol is made from an initiator selected from the group consisting of an alkanolamine, an alkyleneamine, an arylamine, sucrose, glycerin, sorbitol, a methylglucoside, a resin of phenol, aniline and phenol aniline, a Mannich condensate, and mixtures thereof.

15. The method of claim 14 wherein the polyether polyol is made by reacting the initiator with an alkylene oxide.

16. The method of claim 15 wherein the alkylene oxide reacted with the initiator to make the polyether polyol is selected from the group consisting of ethylene oxide, propylene oxide, butylene oxide and mixtures thereof.

17. A method for preparing a polyol useful in the preparation of both polyurethane and polyisocyanurate foams, comprising reacting an ester of phthalic acid having the formula:

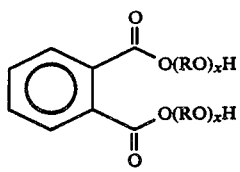

where R is an alkylene moiety of from 2 to 4 carbon atoms, or R is an alkyl moiety, and x ranges from 1 to 4, with two moles of a polyether polyol, where the polyether polyol by reacting an initiator selected from the group consisting of an alkanolamine, an alkyleneamine, an arylamine, sucrose, glycerin, sorbitol, a methylglucoside, a resin of phenol, aniline and phenol aniline, a Mannich condensate, and mixtures thereof, with an alkylene oxide selected from the group consisting of ethylene oxide, propylene oxide and butylene oxide.

18. A polyol useful in the preparation of both polyurethane and polyisocyanurate foams, prepared by a process comprising reacting a phthalic acid derivative with a polyether polyol, where the phthalic acid derivative is selected from the group consisting of phthalic acid, phthalic anhydride and an ester of phthalic acid and where the polyether polyol is made from an initiator selected from the group consisting of an alkanolamine, an alkyleneamine, an arylamine, sucrose, glycerin, sorbitol, a methylglucoside, a resin of phenol, aniline and phenol aniline, a Mannich condensate, and mixtures thereof.

19. A polyol useful in the preparation of both polyurethane and polyisocyanurate foams, prepared by a process comprising reacting a phthalic acid derivative selected from the group consisting of

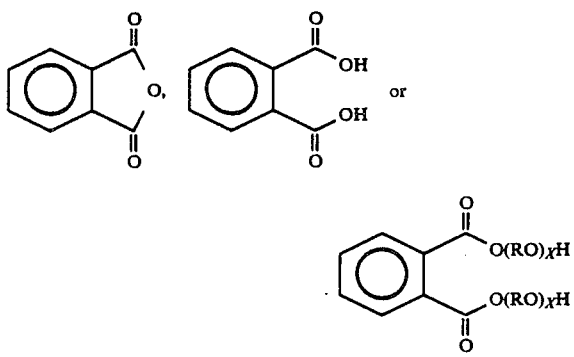

where R is an alkylene moiety of from 2 to 4 carbon atoms or R is an alkyl moiety, and x ranges from 1 to 4, with a polyether polyol made from an initiator selected from the group consisting of an alkanolamine, an alkyleneamine, an arylamine, sucrose, glycerin, sorbitol, a methylglucoside, a resin of phenol, aniline and phenol aniline, a Mannich condensate, and mixtures thereof.

20. A polyol useful in the preparation of both polyurethane and polyisocyanurate foams, prepared by a process comprising the steps of:
reacting a phthalic acid derivative with a polyether polyol where the phthalic acid derivative is selected from the group consisting of phthalic acid and phthalic anhydride and where the polyether polyol is made by alkoxylating an initiator selected from the group consisting of an alkanolamine, an alkyleneamine, an arylamine, sucrose, glycerin, sorbitol, a methylglucoside, a resin of phenol, aniline and phenol aniline, a Mannich condensate, and mixtures thereof, to give an intermediate compound; and
reacting the intermediate compound with an alkylene oxide or an alkylene carbonate to give the polyol useful in preparing foams.

21. A polyol useful in the preparation of both polyurethane and polyisocyanurate foams, prepared by a process comprising reacting one mole of a phthalic acid derivative with two moles of a polyether polyol where the phthalic acid derivative is selected from the group consisting of phthalic acid and phthalic anhydride and where the polyether polyol is made by reacting an alkylene oxide with an initiator selected from the group consisting of an alkanolamine, an alkyleneamine, an arylamine, sucrose, glycerin, sorbitol, a methylglucoside, a resin of phenol, aniline and phenol aniline, a Mannich condensate, and mixtures thereof.

22. A polyol useful in the preparation of both polyurethane and polyisocyanurate foams, made by a process comprising reacting an ester of phthalic acid having the formula:

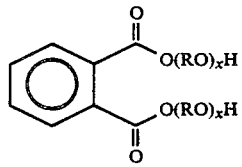

where R is an alkylene group of 2 to 4 carbon atoms, or R is an alkyl moiety, and x ranges from 1 to 4, with a polyether polyol, where the polyether polyol is made from an initiator selected from the group consisting of an alkanolamine, an alkyleneamine, an arylamine, sucrose, glycerin, sorbitol, a methylglucoside, a resin of phenol, aniline and phenol aniline, a Mannich condensate, and mixtures thereof.

* * * * *